United States Patent
Gu et al.

(10) Patent No.: US 7,268,144 B2
(45) Date of Patent: *Sep. 11, 2007

(54) REGIOSPECIFIC SYNTHESIS OF RAPAMYCIN 42-ESTER DERIVATIVES

(75) Inventors: Jianxin Gu, River Edge, NJ (US); Ping Cai, New City, NY (US); Mark E. Ruppen, Garnerville, NY (US)

(73) Assignee: Wyeth, Madison, NJ (US)

( * ) Notice: Subject to any disclaimer, the term of this patent is extended or adjusted under 35 U.S.C. 154(b) by 71 days.

This patent is subject to a terminal disclaimer.

(21) Appl. No.: 11/103,799

(22) Filed: Apr. 12, 2005

(65) Prior Publication Data

US 2005/0234234 A1 Oct. 20, 2005

Related U.S. Application Data

(60) Provisional application No. 60/561,926, filed on Apr. 14, 2004.

(51) Int. Cl.
C07D 498/18 (2006.01)
A61K 31/395 (2006.01)

(52) U.S. Cl. ..................... 514/291; 540/456
(58) Field of Classification Search ............... 540/456; 514/291
See application file for complete search history.

(56) References Cited

U.S. PATENT DOCUMENTS

| 3,929,992 | A | 12/1975 | Sehgal et al. |
|---|---|---|---|
| 4,316,885 | A | 2/1982 | Rakhit |
| 4,650,803 | A | 3/1987 | Stella et al. |
| 5,100,883 | A | 3/1992 | Schichser |
| 5,118,677 | A | 6/1992 | Caufield |
| 5,118,678 | A | 6/1992 | Kao et al. |
| 5,233,036 | A | 8/1993 | Hughes |
| 5,260,300 | A | 11/1993 | Hu |
| 5,362,718 | A | 11/1994 | Skotnicki et al. |
| 6,277,983 | B1 | 8/2001 | Shaw et al. |
| 6,432,973 | B1 | 8/2002 | Zhu et al. |
| 2005/0033046 | A1 | 2/2005 | Chew et al. |
| 2005/0049271 | A1 | 3/2005 | Benjamin et al. |
| 2005/0152983 | A1 | 7/2005 | Ashraf et al. |

FOREIGN PATENT DOCUMENTS

| EP | 0 464 895 | 1/1992 |
|---|---|---|
| EP | 0781 776 B1 | 3/2003 |
| WO | WO92/05179 | 4/1992 |
| WO | WO95/28406 A1 | 10/1995 |
| WO | WO 01/23395 A2 | 4/2001 |
| WO | WO 02/24706 A2 | 3/2002 |
| WO | WO 04/011000 A1 | 2/2004 |
| WO | WO 05/016935 A2 | 2/2005 |

OTHER PUBLICATIONS

M. Adamczyk, et al., Lipase Mediated Hydrolysis of Rapamycin 42-Hemisuccinate Benzyl and Methyl Esters, Tetrahedron Letters, Feb. 14, 1994, pp. 1019-1022, Vo. 35, No. 7, Elsevier Science Ltd., Great Britain.

McGraw-Hill Dictionary of Scientific and Technical Terms, 3rd ed. (1984), p. 996.

*Primary Examiner*—Bruck Kifle
(74) *Attorney, Agent, or Firm*—Arnold S. Milowsky; Howson & Howson LLP

(57) ABSTRACT

A method for the regiospecific synthesis of rapamycin 42-ester derivatives is described. The method involves lipase-catalyzed acetylation of 42-hydroxy of rapamycin with an acyl donor such as a vinyl ester, an isopropenyl ester or an anhydride in a suitable organic solvent.

14 Claims, No Drawings

REGIOSPECIFIC SYNTHESIS OF RAPAMYCIN 42-ESTER DERIVATIVES

CROSS-REFERENCE TO RELATED APPLICATIONS

This application claims the benefit under 35 USC 119(e) of prior U.S. Provisional Patent Application No. 60/561,926, filed Apr. 14, 2004.

BACKGROUND OF THE INVENTION

Rapamycin (Rapamune®) is an immunosuppressant derived from nature, which has a novel mechanism of action. CCI-779 (rapamycin 42-ester with 3-hydroxy-2-(hydroxymethyl)-2-methylpropionic acid) is an ester of rapamycin, which has demonstrated significant inhibitory effects on tumor growth in both in vitro and in vivo models.

Modification of rapamycin has mainly focused on production of its 42-hydroxy ester derivatives. These 42-hydroxy rapamycin ester derivatives are useful for inducing immunosuppression, and in the treatment of transplantation rejection, autoimmune diseases, diseases of inflammation, adult T-cell leukemia/lymphoma, solid tumors, fungal infections, et al.

Esterification of rapamycin at the 42-position has been performed by directly reacting rapamycin with acylating agents. However, as rapamycin contains two secondary hydroxyl groups at positions 31 and 42, attempts to discriminate between these two hydroxyl groups in order to achieve a regioselective synthesis of 42-monoacylated products posed a difficult challenge.

A number of patents involving the synthesis of 42-acylated derivatives have been issued, such as alkyl ester (U.S. Pat. No. 4,316,885), aminoalkyl esters (U.S. Pat. No. 4,650,803), fluorinated esters (U.S. Pat. No. 5,100,883), amide esters (U.S. Pat. No. 5,118,677), carbamate esters (U.S. Pat. No. 5,118,678), alkoxyesters (U.S. Pat. No. 5,233,036), carbonate esters (U.S. Pat. No. 5,260,300), hydroxyesters (U.S. Pat. Nos. 5,362,718 & 6,277,983). However, none of the patents described methods that are stereospecific. Further, the yields for 42-monoesters of rapamycin produced by these methods are typically poor to moderate due to the poor regioselectivity and instability of rapamycin molecule in basic or acidic conditions. High performance liquid chromatography (HPLC) separation is usually required in order to get the pure product. One solution proposed for improving the regioselectivity is the use of 31-silyl protected rapamycin as an intermediate. However, this method adds several more steps of manipulation.

What is needed is an efficient method for synthesis of rapamycin esters.

SUMMARY OF THE INVENTION

The invention provides a lipase-catalyzed synthesis of rapamycin 42-ester derivatives. The remarkable features of this simple process are regiospecificity and excellent yield under mild conditions.

Other aspects and advantages of the invention will be readily apparent to one of skill in the art.

DETAILED DESCRIPTION OF THE INVENTION

The present invention provides a process for preparing rapamycin 42-esters of the general formula (I) in a regiospecific fashion using lipase in the presence of a rapamycin and an acyl donor.

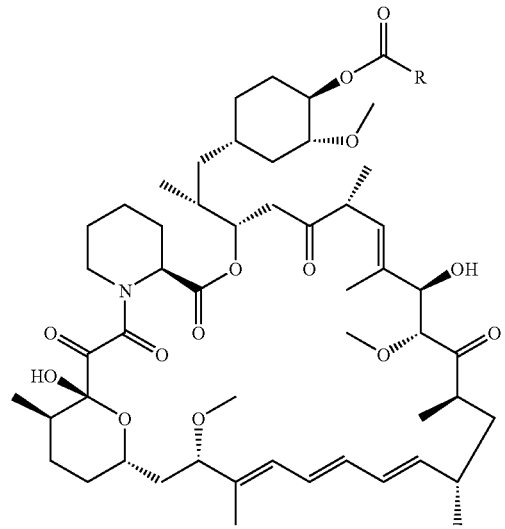

(I)

wherein, R is a linear or cyclic, aliphatic or aromatic, saturated or unsaturated hydrocarbon which optionally contains a hydroxyl, halogen and/or thio substituent(s). In one embodiment, the halogen is Cl, Br, I or F.

Rapamycin can be prepared as previously described. See, e.g., U.S. Pat. No. 3,929,992, issued Dec. 30, 1975. Alternatively, rapamycin may be purchased from commercial sources [e.g. Rapamune® (Wyeth)] or prepared using alternative methods. The means of preparing, purifying and/or obtaining the rapamycin starting material are not a limitation of the present invention.

In one embodiment, the invention provides a regiospecific route for production of ketal-protected rapamycin 42-esters, useful in production of a rapamycin 42-ester. In a further embodiment, the invention provides for the production of isopropylidene ketal protected rapamycin 42-ester with 3-hydroxy-2-(hydroxymethyl)-2-methylpropionic acid, a precursor of CCI-779. CCI-779 is an ester of rapamycin which has demonstrated significant inhibitory effects on tumor growth in both in vitro and in vivo models. The use of this and other hydroxyesters of rapamycin are described in U.S. Pat. Nos. 5,362,718 and 6,277,983, and U.S. Patent Publication No. US 2005-0033046 A1 (U.S. patent application Ser. No. 10/903,062).

The removal of the ketal protecting group can be accomplished under mildly acidic conditions. In general, the procedure published in U.S. Pat. No. 6,277,983 and documents cited therein can be followed. In one embodiment, the deprotection is carried out in a single phase aqueous acid/organic solvent system, e.g., diluted sulfuric acid in tetrahydrofuran (THF), such as 2 N $H_2SO_4$/THF at about 0 to 5° C. However, this reaction can take about 3 days or more to complete and solvent extraction is needed to recover the product from aqueous media after the reaction is complete. Other procedures for removal of the ketal protecting group would be known to one of ordinary skill in the art, such as those described in the International Patent Application entitled *Proline CCI-*779, *Production and Uses Therefor, and Two Step Enzymatic Synthesis of Proline CCI-*779 *and CCI-*779 (Chew, et al., based on U.S. Provisional Patent Application Nos.: 60/562,069 (filed Apr. 14, 2004) and 60/623,594 (filed Oct. 29, 2004)).

As used herein, "microbial lipases" include enzymes which catalyze the hydrolysis and formation of ester bonds, which were originally isolated from a non-eukaryotic source, such as, *Aspergillus niger, Candida antarctica, Candida rugosa, Mucor miehei, Pseudomonas cepacia, Pseudomonas fluorescens, Rhizopus delemar*, inter alia. However, the enzyme selected for use in the invention need not be directly isolated and purified from the original source, but can be prepared synthetically or recombinantly, or through other suitable means. A variety of these enzymes are available from some commercial sources, further, these enzyme preparations can be used as crude, partially purified, purified or immobilized from different microbial origin under different trade names by various suppliers.

In one embodiment, the lipase from *Candida antarctica*, type B is used in the practice of this invention. Of all the lipases studied to date, this lipase provides the highest conversion rates and highest isolated yields. *C. antarctica* lipase is commercially available, e.g., under the product designation NOVO SP435 or NOVOZYME 435 from Novo Nordisk, or CHIRAZYME L-2 from Roche Molecular Biochemicals and BioCatalytics.

Lipase PS, from *Pseudomonas cepacia*, particularly its immobilized form, lipase PS-C [e.g., which is available as "Amano" II lipase from Amano], can perform the reaction equally well as NOVOZYM 435 lipase from the synthetic point of view, although at slower reaction rate. For the process of the invention, the microbial (e.g., *C. antarctica* (type B)) lipase is combined with a suitable solvent for catalysis of the reaction between an acyl donor and rapamycin. One of skill in the art can readily select a suitable solvent from among, e.g., toluene, tert-butyl methyl ether (TBME), ethyl ether, THF, MeCN, $CH_2Cl_2$, $CHCl_3$, hexane, dioxane, or mixtures including these solvents. In one embodiment, TBME (tert-butyl methyl ether) is used. The acyl donor utilized in the method of the invention is selected from among several activated esters such as vinyl esters, isopropenyl esters and anhydrides.

In one embodiment, the vinyl esters are selected from among esters of the formula $CH_2=CH-O-COR^1$, where $R^1$ is an alkyl, alkenyl, aryl, benzyl, either unsubstituted or substituted with hydroxyl, halogen (F, Cl, Br, I) and thio. Suitable vinyl esters include vinyl acetate, vinyl propionate, vinyl chloroacetate, vinyl crotonate, vinyl benzoate, and vinyl decanoate. However, other suitable vinyl esters can be readily selected by one of skill in the art.

In one embodiment, isopropenyl esters are selected from among esters of the formula $CH_2=C(CH_3)-OCOR^2$, where $R^2$ is an alkyl, alkenyl, aryl, benzyl, either unsubstituted or substituted with hydroxyl, halogen (F, Cl, Br, I) and thio. In another embodiment, the acyl donor is isopropenyl acetate.

The term "alkyl" is used herein to refer to both straight- and branched-chain saturated aliphatic hydrocarbon groups having one to ten carbon atoms, preferably one to eight carbon atoms and, most preferably, one to six carbon atoms.

The term "alkenyl" is intended to include both straight- and branched-chain alkyl group with at least one carbon-carbon double bond and two to eight carbon atoms, preferably two to six carbon atoms.

The term "aryl" is used herein to refer to a carbocyclic aromatic system, which may be a single ring, or multiple aromatic rings fused or linked together as such that at least one part of the fused or linked rings forms the conjugated aromatic system, e.g., of 6 to 14 carbon atoms. The aryl groups include, but are not limited to, phenyl, naphthyl, biphenyl, anthryl, tetrahydronaphthyl, phenanthryl, and indane.

The term "benzyl" is used herein to refer to a group of formula $C_6H_5CH_2$.

Suitable anhydrides are readily selected from among alkanoic anhydrides (i.e., $C_1$, $C_2$, $C_3$, $C_4$, $C_5$, $C_6$, $C_7$ and $C_8$ anhydrides), which may be branched or straight-chained, or substituted with halogen, hydroxyl.

In one embodiment, the enzymatic process of the invention can be carried out in the range of about 20° C. to about 75° C., or about 25° C., 27° C., 30° C., 40° C. to about 70° C., or about 32° C. or about 37° C. to about 65° C. In another embodiment, the temperature is about 30° C. to about 55° C. In yet another embodiment, the temperature is about room temperature to about 45° C. Typically, the reaction is performed under $N_2$ until all starting material is consumed. The reaction can be monitored by various techniques such as thin layer chromatography (TLC) and high performance liquid chromatography (HPLC). Alternatively, other monitoring methods can be used by one of skill in the art.

In a reaction utilizing a vinyl ester or isopropenyl ester as the acyl donor, the enzyme (lipase) is filtered off and washed with a suitable solvent. The solvent may be the same as selected for use in the reaction, or may differ from the solvent in the reaction. Where the solvent differs, it can be chosen from among the solvents defined above, or other commonly-used solvents, such as acetone, ethyl acetate, methanol, ethanol, isopropanol, among others. The combined organic solvent can then be evaporated off under suitable conditions, e.g., reduced pressure. The residue is then purified by suitable means, e.g., by silica gel column chromatography, eluting with a suitable solvent, or recrystallization with a suitable solvent (e.g., hexane-acetone, hexane-ethyl acetate, ethyl ether, among others). Other suitable purification means are known to those of skill in the art. Further, other suitable solvent mixtures and ratios can be readily determined by one of skill in the art.

In another embodiment, anhydrides are used as acyl donors in the enzyme-catalyzed preparation of 42-ester derivatives. In a further embodiment, yields approximately 95%. (Examples 10-12). In such an embodiment, the anhydride and suitable amount of enzyme are mixed in a suitable solvent with rapamycin, and stirred for about 16 to 96 hours, and more preferably, about 24 hours to 48 hours in the presence of $N_2$, protected from light. Suitably, the reaction is performed at about room temperature to about 50° C. The amount of enzyme (w/w) to rapamycin can vary based on the kind of anhydride and length of reaction, e.g., from approximately equivalent amounts (on a weight basis) of rapamycin and enzyme (w/w) to excess amounts of enzyme in order to drive the reaction more quickly. Optionally, if the reaction does not finish after certain period time as stated above, additional enzyme can be added, and the mixture stirred for a further period of time until the reaction was completed as judged by TLC or HPLC. After the enzyme is removed via filtration, the solvent is then removed under reduced pressure. The residue is purified using suitable techniques, e.g., by silica gel column chromatography or recrystallization.

The regiospecific rapamycin 42-derivatives of the invention are useful in pharmaceutical compositions. Thus, the rapamycin 42-derivatives of the invention can be formulated by any suitable method described in the art for rapamycin or derivatives thereof.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The parenteral formulations useful in this invention can be used to produce a dosage form that is suitable for administration by either direct injection or by addition to sterile infusion fluids for intravenous infusion.

Transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The present invention further provides packaging and kits containing the regiospecific rapamycin 42-derivatives produced according to the present invention and formulated for administration by a suitable delivery method. In one embodiment, the regiospecific rapamycin 42-derivatives are present in unit dosage form. Suitable containers, including bottles, vials, blister packs, and the like are known to those of skill in the art. Such packaging and kits may further contain other components, including, e.g., instructions for use, syringes, applicators, and the like.

The following examples are illustrative of the methods of the invention for regiospecific production of rapamycin 42-ester derivatives. As illustrated in the following examples, *Candida antarctica* lipase is particularly well suited in its ability to catalyze transesterification of rapamycin to its 42-acyl derivative using vinyl acetate as acyl donor. However, as stated above, the invention is not so limited and other suitable lipases of microbial origin can be utilized. For example, lipase PS, from *Pseudomonas cepacia* and its immobilized form, lipase PS-C "Amano"II, Lipase PS-D the reaction conditions can include higher temperature with more enzyme. For example, in one embodiment utilizing immobilized lipase PS-C, double the amount of lipase (i.e., 200% of rapamycin (W/W) is required to achieve the conversion rate of NOVOZYM 435 lipase at room temperature; alternatively, the temperature can be raised to about 45° C. when less amount of enzyme (100% (w/w) to rapamycin) is used).

EXAMPLES

The following examples illustrate the process of the invention, using vinyl ester (Examples 1-8), isopropenyl ester (Example 9) or an anhydride (Examples 10-12).

In one embodiment, a mixture of rapamycin (20 mg, 0.022 mmol), vinyl ester (50 μL) and NOVOZYM 435 lipase (20 mg) in TBME (0.5 mL) was stirred at room temperature (rt) or 45° C. under $N_2$ until all starting material was consumed monitored by TLC. The enzyme was filtered off and washed with TBME. The combined organic solvent was evaporated under reduced pressure. The residue was purified by silica gel column chromatography eluting with hexane-acetone (2:1, v/v) or recrystallized from hexane-acetone. Additional examples are illustrated in the schemes below.
Example 1
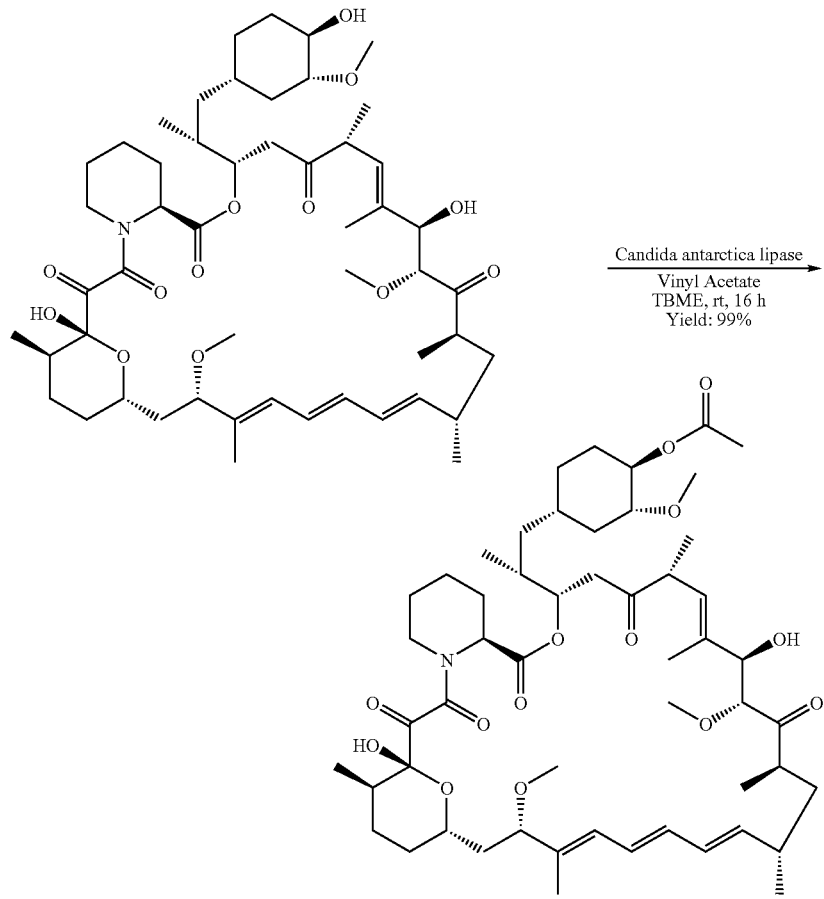
Example 2
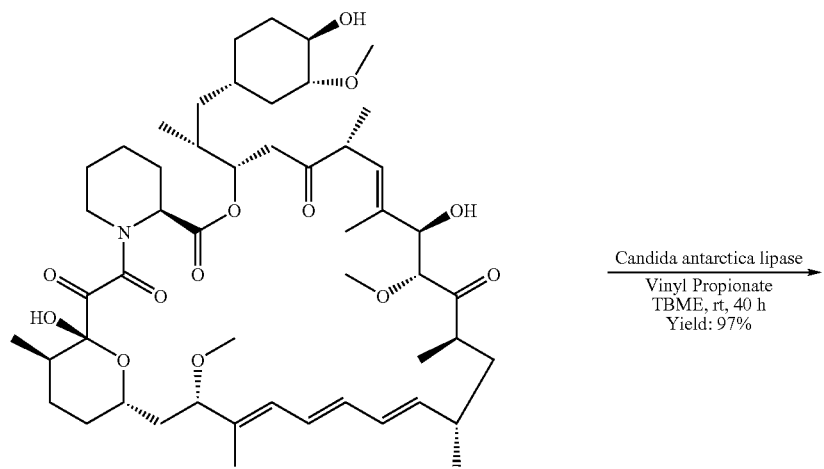

-continued
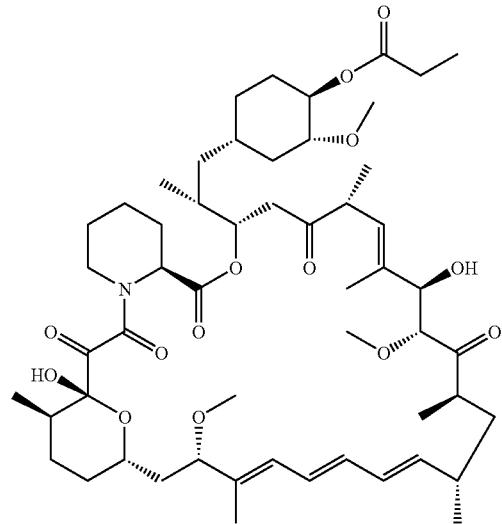
Example 3
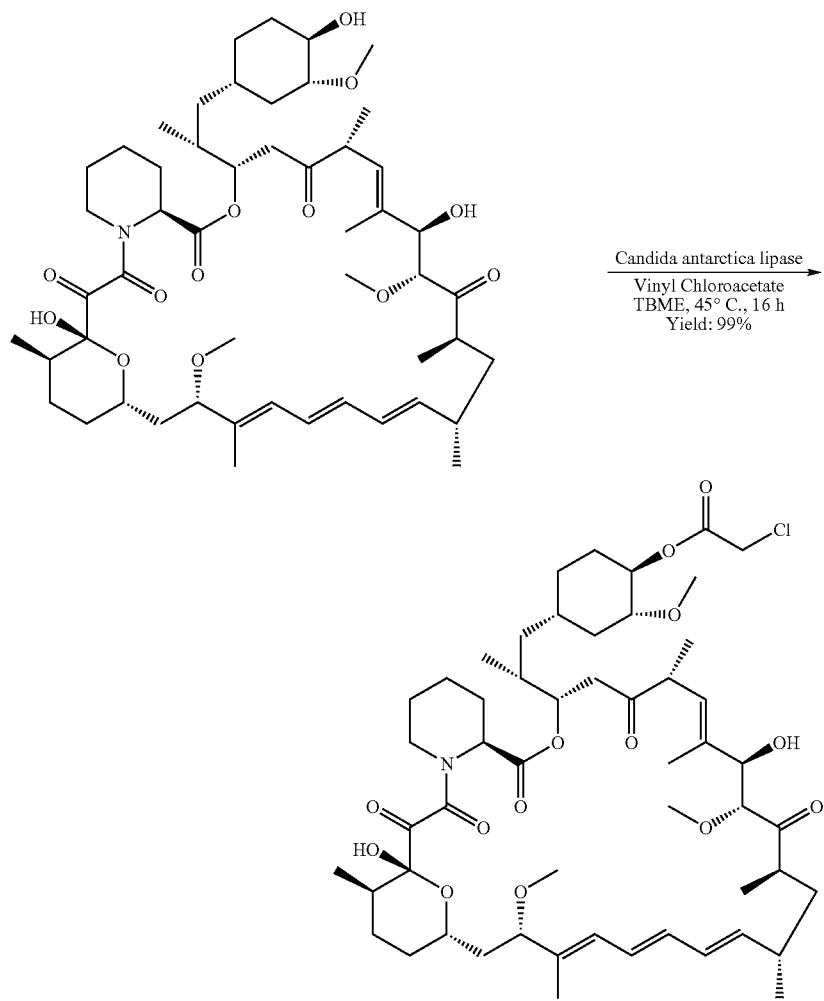

Example 4
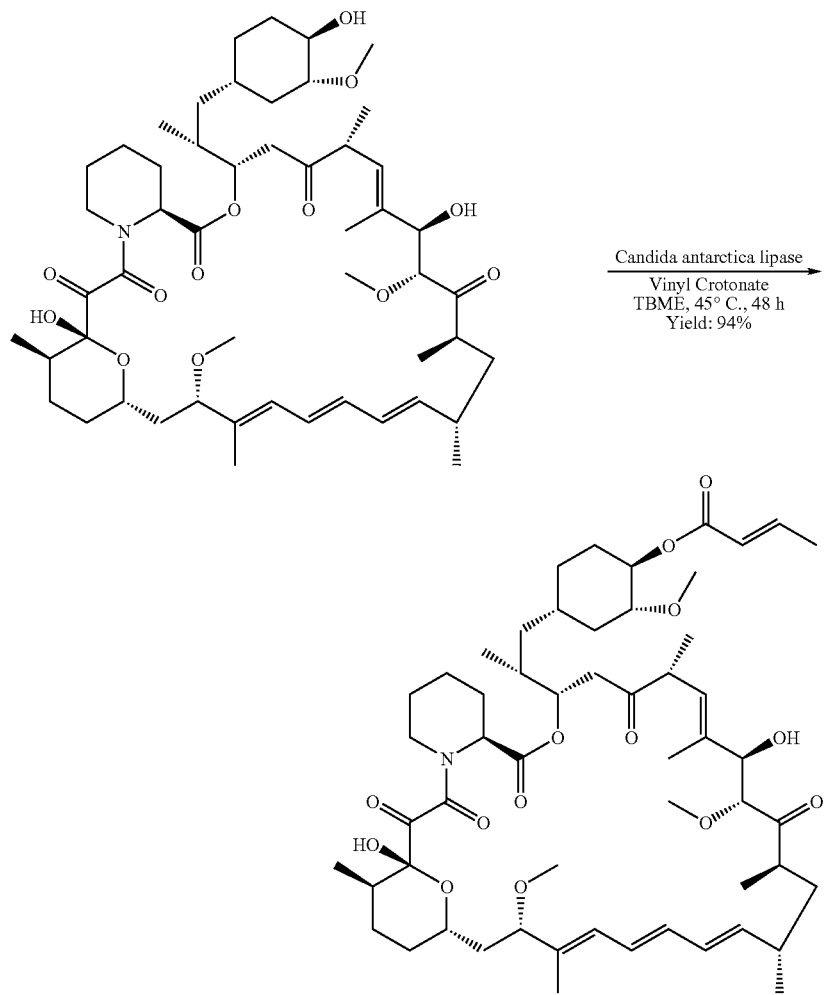
Example 5
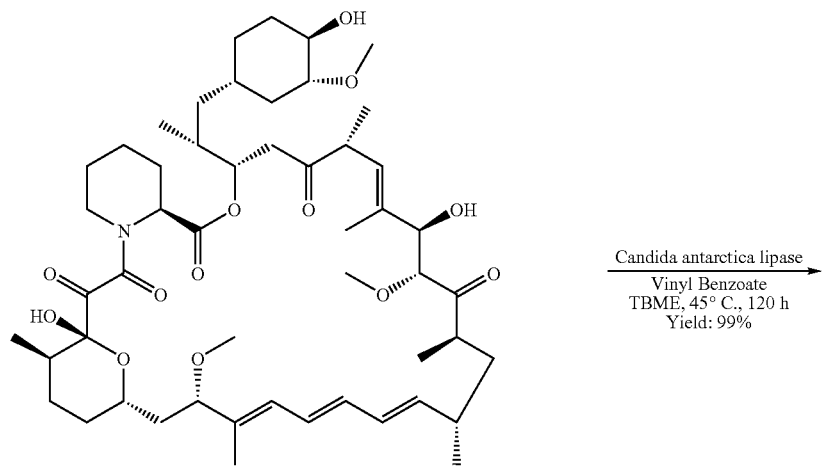

-continued
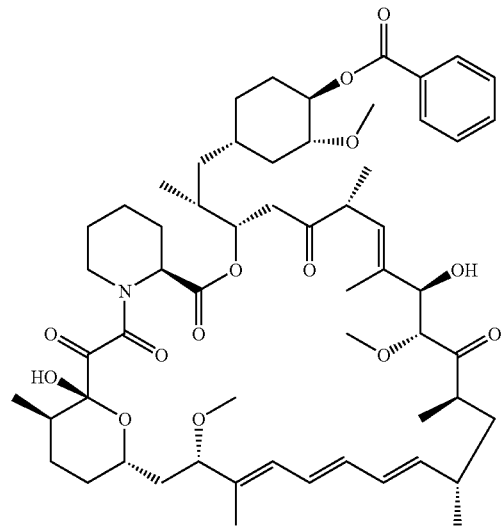
Example 6
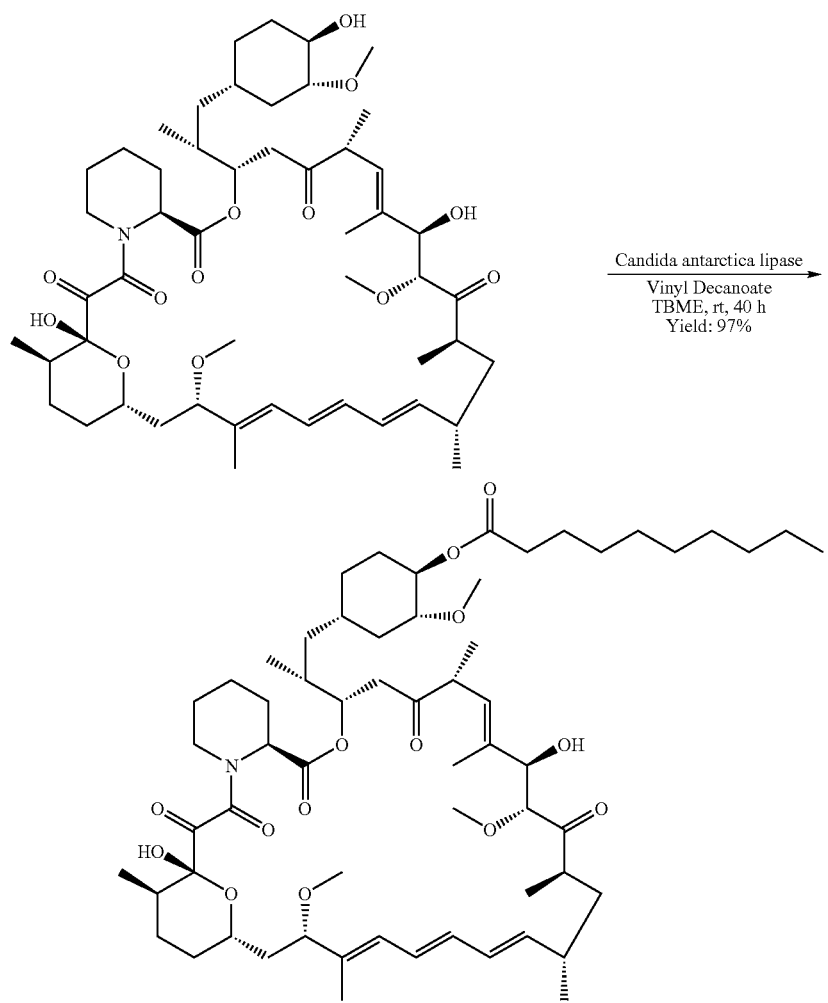

Example 7
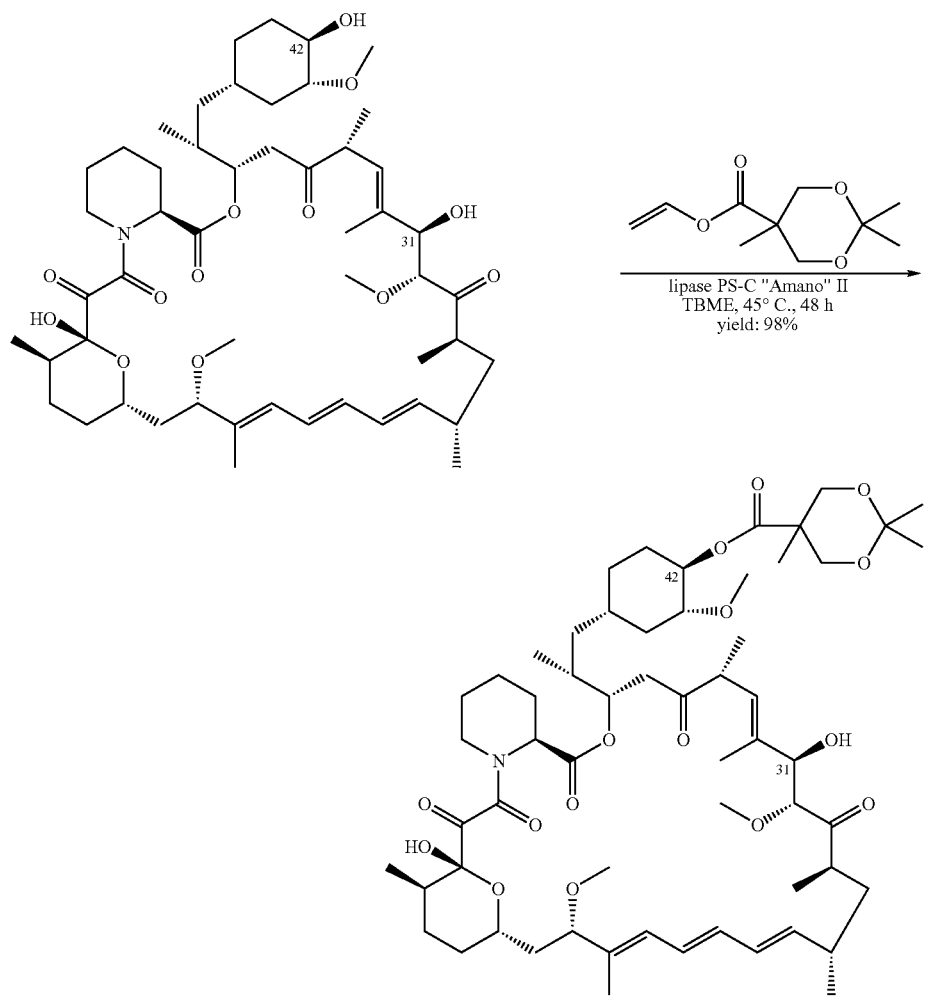
Example 8
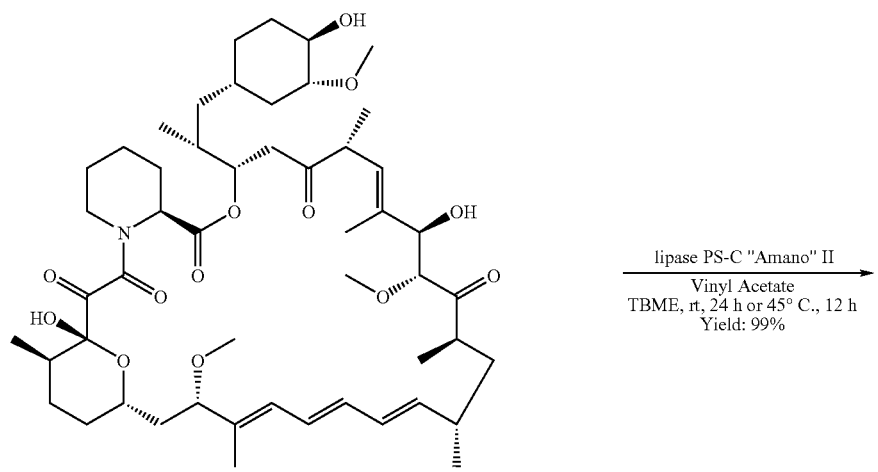

-continued
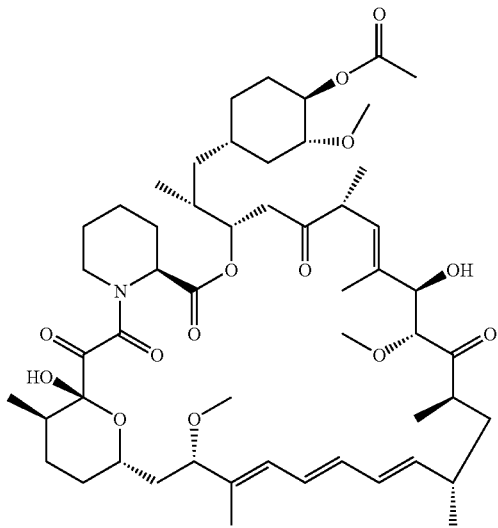
Example 9
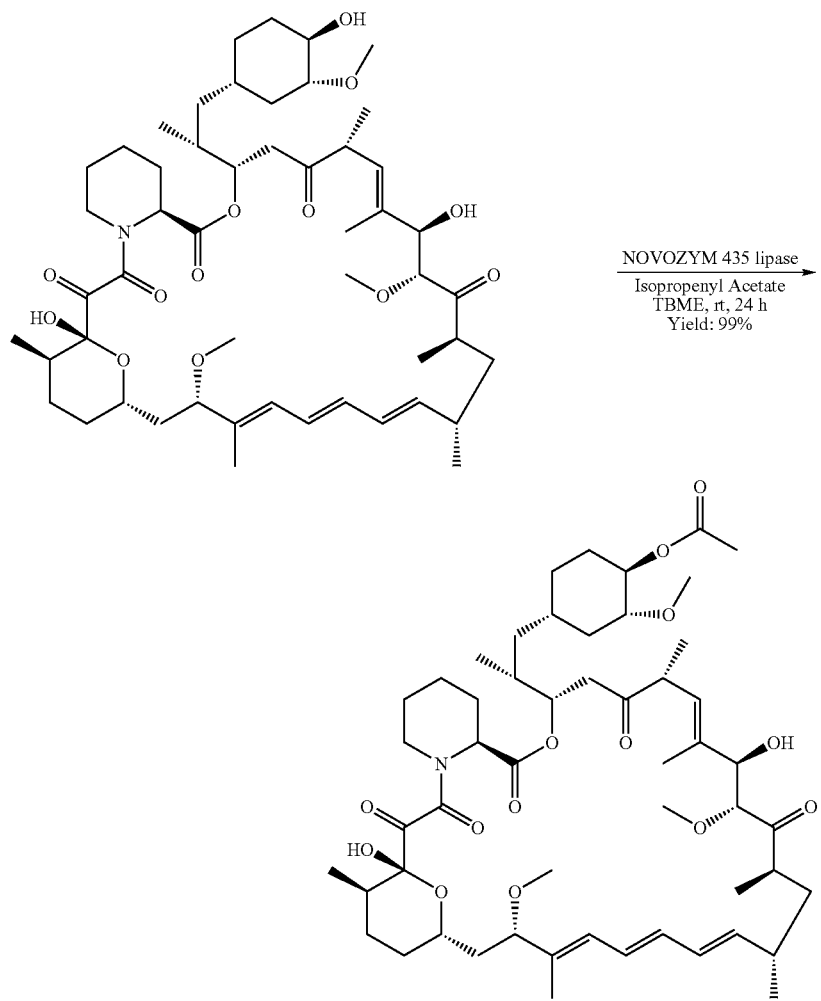

Rapamycin 42-ester derivatives using anhydrides as the acyl donor are prepared according to the invention as follows.

A mixture of rapamycin (20 mg, 0.022 mmol), anhydride (30 mg) and NOVOZYM 435 lipase (20 mg) in TBME (0.5 mL) were stirred at room temperature for 48 h ($N_2$, protected from light). [In the case of acetic anhydride or propionic anhydride, after 48 h, another portion of NOVOZYM 435 lipase (20 mg) and TBME (0.1 mL) was added and the mixture was stirred another 48 h before the reaction was quenched]. The solvent was then removed by flushing with $N_2$ gas. The residue was purified by silica gel column chromatography eluting with hexane-acetone (2:1, v/v). The product was isolated as a white solid.

Example 10

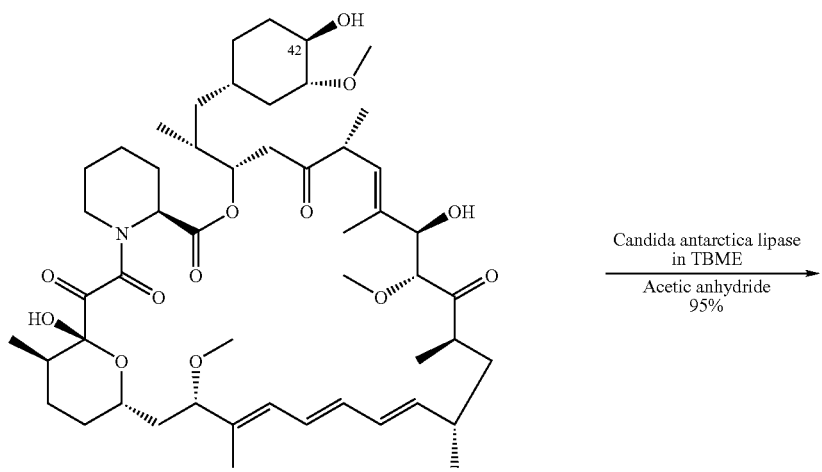

Candida antarctica lipase
in TBME
Acetic anhydride
95%

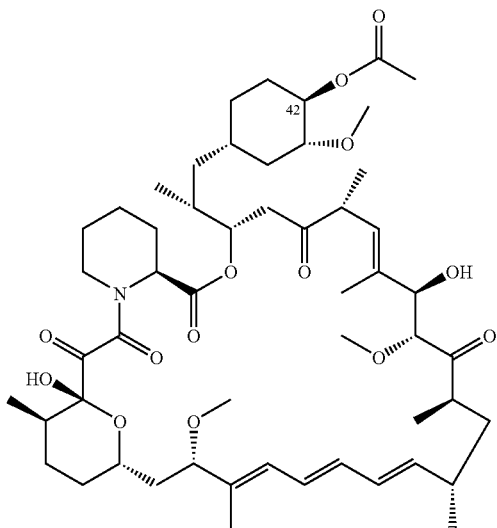

Example 11
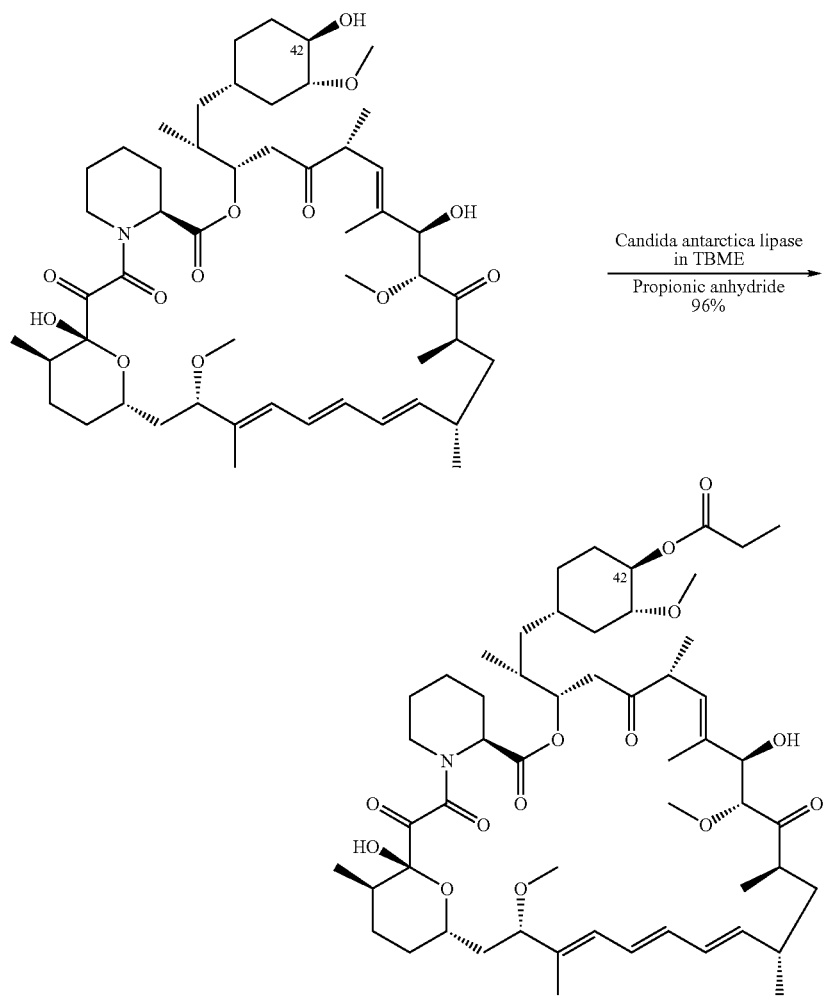
Example 12
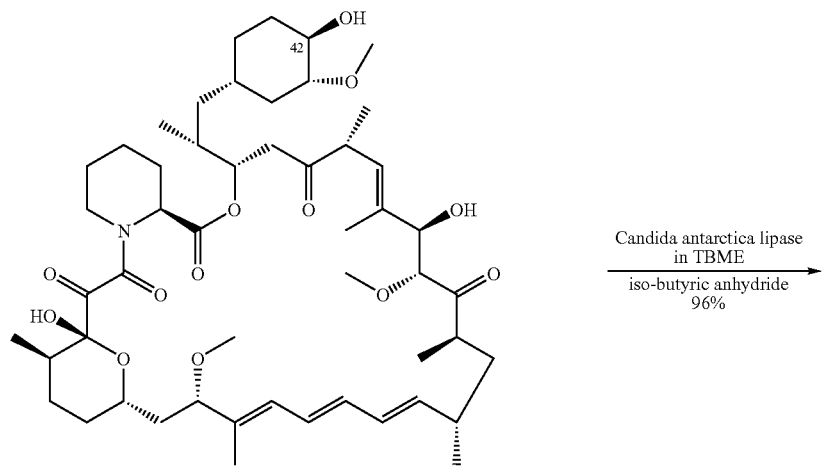

-continued

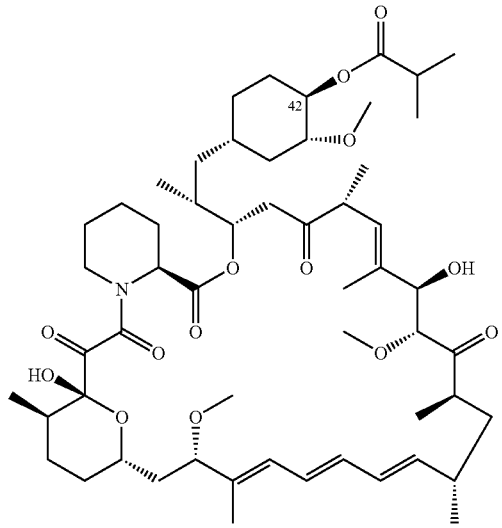

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are listed throughout this application, the disclosures of which are incorporated herein by reference in their entireties. To the extent that a conflict may exist between the specification and a document listed herein, the language of the disclosure made herein controls.

What is claimed is:

1. A method for the regiospecific preparation of a rapamycin 42-ester of the formula (I)

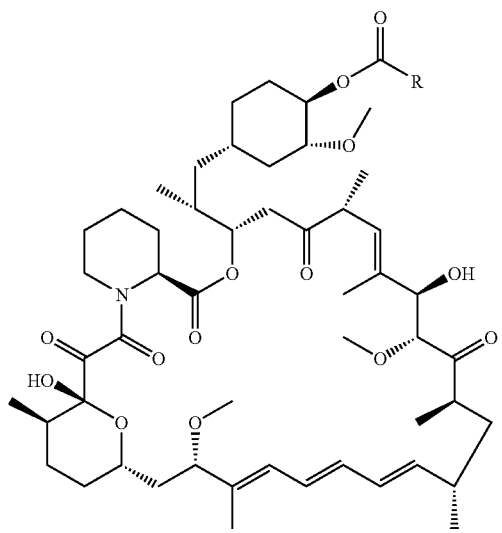

(I)

wherein R is a linear or cyclic, aliphatic or aromatic, saturated or unsaturated hydrocarbon which optionally contains a hydroxyl, halogen and/or thiol substituent(s), said method comprising acylating a 42-hydroxy rapamycin with a lipase in the presence of an acyl donor.

2. The method according to claim 1, wherein the lipase used is a microbial lipase from a microorganism selected from the group consisting of *Aspergillus niger, Candida antarctica, Candida rugosa, Mucor miehei, Pseudomonas cepacia, Pseudomonas fluorescens*, and *Rhizopus delemar*.

3. The method according to claim 2, wherein the lipase used is from *Candida antarctica* type B (NOVOZYM 435 lipase) or *Pseudomonas cepacia* (lipase PS-C "Amano" II).

4. The method according to claim 1, wherein the acyl donor is a vinyl ester, an isopropenyl ester or an anhydride.

5. The method according to claim 4 wherein the vinyl ester has the formula $CH_2=CH-O-COR_1$, wherein $R^1$ is selected from the group consisting of $C_1$-$C_{10}$ alkyl, $C_2$-$C_8$ alkenyl, $C_6$-$C_{14}$ aryl, benzyl, optionally substituted with a group independently selected from hydroxyl, halogen and SH.

6. The method according to claim 1 wherein the vinyl ester is selected from the group consisting of vinyl acetate, vinyl propionate, vinyl chloroacetate, vinyl crotonate, vinyl benzoate, and vinyl decanoate.

7. The method according to claim 4 wherein the vinyl ester is isopropylidene protected vinyl 3-hydroxy-2-(hydroxymethyl)-2-methylpropionate.

8. The method according to claim 4 wherein the isopropenyl ester has the formula $CH_2=C(CH_3)-OCOR^2$, wherein $R^2$ is selected from the group consisting of $C_1$-$C_{10}$ alkyl, $C_2$-$C_8$ alkenyl, $C_6$-$C_{14}$ aryl, benzyl, optionally substituted with a group independently selected from hydroxyl, halogen and —SH.

9. The method according to claim 8 wherein the isopropenyl ester is isopropenyl acetate.

10. The method according to claim 4 wherein the anhydride is a $C_1$-$C_8$ straight-chain or branch-chain alkanoic anhydride, optionally substituted with a group independently selected from halogen and hydroxyl.

11. The method according to claim 1, wherein the reaction takes place in an organic solvent is selected from the group consisting of toluene, tert-butyl methyl ether (TBME), ethyl ether, THF, MeCN, CH$_2$Cl$_2$, CHCl$_3$, hexane, dioxane or mixtures thereof.

12. The method according to claim 1, wherein the reaction is conducted in the range of 20° C. to 75° C.

13. A regiospecific rapamycin 42-ester with isopropylidene ketal protected 3-hydroxy-2-(hydroxymethyl)-2-methylpropionic acid, a precursor of (-rapamycin 42-ester with 3-hydroxy-2-(hydroxymethyl)-2-methylpropionic acid, CCI-779).

14. A pharmaceutical kit comprising units of a regiospecific rapamycin 42-derivative produced according to claim 1 in unit dosage form.

* * * * *